US00PP35369P2

(12) United States Plant Patent
Bacon et al.

(10) Patent No.: US PP35,369 P2
(45) Date of Patent: Sep. 5, 2023

(54) GRAPEVINE PLANT NAMED 'SUGRA62'

(50) Latin Name: *Vitis vinifera*
Varietal Denomination: Sugra62

(71) Applicant: Sun World International, LLC, Bakersfield, CA (US)

(72) Inventors: Terry A. Bacon, Maplewood, NJ (US); Terrence J. Frett, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 18/093,744

(22) Filed: Jan. 5, 2023

(51) Int. Cl.
*A01H 5/08* (2018.01)
*A01H 6/88* (2018.01)

(52) U.S. Cl.
USPC ..... Plt./207
CPC ..... *A01H 6/88* (2018.05)

(58) Field of Classification Search
USPC ..... Plt./207
CPC ..... A01H 5/0812
See application file for complete search history.

(56) References Cited

U.S. PATENT DOCUMENTS

PP3,106 P * 4/1972 Garabedian ..... Plt./207

* cited by examiner

*Primary Examiner* — Kent L Bell
(74) *Attorney, Agent, or Firm* — Knobbe, Martens, Olson & Bear, LLP

(57) ABSTRACT

The new variety of grapevine 'Sugra62' is characterized by the production of a large-sized, green and broad elliptic berry with a very early season ripening date. The berries of 'Sugra62' are very firm and very juicy.

1 Drawing Sheet

Latin name of the genus and species claimed: *Vitis vinifera.*

Variety denomination: 'Sugra62'.

BACKGROUND AND SUMMARY OF THE INVENTION

This application relates to the discovery and asexual propagation of a new and distinct variety of grapevine, 'Sugra62', as herein described and illustrated. The new variety was first selected as breeder number 'GR943W' by Terry A. Bacon and Terrence J. Frett in Wasco, Kern County, Calif. in July 2020. The variety was originated by controlled hybridization.

The new variety 'Sugra62' is characterized by the production of a large-sized, green and broad elliptic berry with a very early season ripening date. The berries of 'Sugra62' are very firm.

The seed parent is 'Sugrafiftytwo' (U.S. Plant Pat. No. 30,664) and the pollen parent is an unknown member of a bulk pollen mixture of four unpatented breeding selections: 'GR708W', 'GR720W', 'GR726W' and 'GR727W'. The parent varieties were first crossed in April 2018. The date of first sowing was March 2019, and the date of first flowering was April 2020.

The new variety 'Sugra62' was first asexually propagated in December 2020 in Wasco, Kern County, Calif., by Terry A. Bacon and Terrence J. Frett using hardwood cuttings.

The new variety 'Sugra62' can be distinguished from each of the four grape varieties of the bulk pollen parent: 'GR708W', 'GR720W', 'GR726W' and 'GR727W'. The fruit of the new variety 'Sugra62' ripens earlier than the fruit of each of 'GR708W', 'GR720W', 'GR726W' and 'GR727W.' Further, the new variety 'Sugra62' has a larger cluster size than 'GR708W' and 'GR726W' at 625 g and a larger berry weight at 8.5 g, compared to a cluster size of 575 g and a berry weight of 7.3 g for 'GR708W', and a cluster size of 600 g and a berry weight of 7.4 g for 'GR726W'. The new variety 'Sugra62' has a smaller cluster size than 'GR720W' and 'GR727W' but a larger berry weight of 8.5 g compared to 7.8 g for 'GR720W' and 7.6 g for 'GR727W.' Additionally, the berries of the new variety 'Sugra62' are broad elliptic compared to the obtuse ovate berries of GR708W', 'GR720W', 'GR726W' and 'GR727W'.

The new variety 'Sugra62' is distinguished from its seed parent 'Sugrafiftytwo' (U.S. Plant Pat. No. 30,664) in that while both varieties have green skin, the ripening of the fruit of the new variety 'Sugra62' starts 2 days earlier than that of 'Sugrafiftytwo'. The new variety 'Sugra62' also has a broad elliptic berry shape compared to the narrow elliptic berry shape of 'Sugrafiftytwo'. Further, the new variety 'Sugra62' has a larger berry weight, at 8.5 g, compared to 7.5 g for 'Sugrafiftytwo'.

The fruit of the new variety 'Sugra62' has a ripening time that is similar to that of 'Flame Seedless' (unpatented), but the new variety 'Sugra62' has broad elliptic green berries, compared to the globose red berries of 'Flame Seedless'.

The fruit of the new variety 'Sugra62' has a green skin and broad elliptic berry shape like that of 'Sugraone' (U.S. Plant Pat. No. 3,106) and 'Sheegene-21' (U.S. Plant Pat. No. 23,837), but ripening of the berries of the new variety 'Sugra62' begins earlier on July 2, compared to July 15 for 'Sugraone' and July 19 for 'Sheegene-21'.

The new 'Sugra62' variety has been shown to maintain its distinguishing characteristics through successive asexual propagations by, for example, cuttings and grafting.

Variations of the usual magnitude from the characteristics described herein may occur with changes in any of a variety of factors such as growing conditions, irrigation, fertilization, pruning, management and climatic variation.

BRIEF DESCRIPTION OF THE DRAWING

The accompanying color photographic illustration taken from a 3-year-old plant shows typical specimens of the foliage and fruit of the present new grape variety 'Sugra62'. The illustration shows the upper and lower surfaces of the leaves and exterior and sectional views of the fruit. The photographic illustration was taken shortly after the fruit was picked and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England, 1986.

Many of the descriptive values in this specification are based on and conform to those set forth by the International Board for Plant Genetic Resources Institute Grape Descriptors (*Vitis* spp.) of 1983 and/or 1997, which was developed in collaboration with the Office International de la Vigne et du Vin (OIV) and the International Union for the Protection of New Varieties of Plants (UPOV).

The descriptive matter which follows pertains to three-year-old 'Sugra62' plants grown in the vicinity of Wasco, Kern County, Calif. during 2022, and is believed to apply to plants of the variety grown under similar conditions of soil and climate elsewhere.

VINE

General: (Measurements taken on a three-year-old plant).

- *Vine size: Large. Height: Approximately* 2.0 m. Width: Approximately 2.5 m.
- *Vigor*.—Medium-high.
- *Density of foliage*.—Dense.
- *Productivity*.—Very productive.
- *Crop load*.—Approximately 26 kg per vine after thinning.
- *Own root*.—Yes.
- *Training method*.—Typically spur pruned leaving about 40 2-bud spurs.
- *Resistance*.—Neither resistance nor susceptibility to particular diseases or pests has been observed in this variety Trunk:

- *Shape*.—Stocky.
- *Diameter*.—Approximately 7.8 cm (at 30 cm above the soil line).
- *Straps*.—Short.
- *Surface texture*.—Medium shaggy.
- *Inner and outer bark color*.—Inner bark about Medium Greyed-Orange 166C and weathering to about Dark Greyed-Green 197B in the outer bark.

SHOOTS

Young shoot:

- *Form of tip*.—Half open.
- *Intensity of anthocyanin coloration of tip*.—Absent or very sparse.
- *Density of prostrate hairs on tip*.—Absent or very sparse.
- *Density of erect hairs on tip*.—Absent or very sparse.
- *Color*.—About Medium Green 139C.

Woody shoot (observations made in the middle third of shoot):

- *Attitude before tying*.—Semi-drooping.
- *Growth of axillary shoots*.—Medium, about 18 to 23 cm in length.
- *Internode length*.—Medium, approximately 70 mm to 90 mm.
- *Width at node*.—Approximately 10 mm.
- *Cross section*.—Circular.
- *Surface texture*.—Striated.
- *Main color*.—About Medium Greyed-Orange 166D.
- *Color of dorsal side of internode*.—About Medium Greyed-Orange 166D.
- *Color of ventral side of internode*.—About Medium Greyed-Orange 166D.
- *Color of dorsal side of node*.—About Medium Greyed-Orange 166D.
- *Color of ventral side of node*.—About Medium Greyed-Orange 166D.
- *Density of erect hairs on nodes*.—Absent.
- *Density of erect hairs on internodes*.—Absent or Very Sparse.
- *Density of prostrate hairs on internodes*.—Absent or Very Sparse.
- *Density of prostrate hairs on nodes*.—Absent or Very Sparse.

Tendrils:

- *Distribution on the shoot at full flowering*.—Continuous.
- *Thickness*.—Approximately 3 mm.
- *Color*.—About Light Green 141D in mid-summer.
- *Form*.—Bifurcated.
- *Number of consecutive tendrils*.—About 2.
- *Length of tendril*.—Medium, approximately 14 cm.

LEAVES

Young leaves:

- *Color of upper surface of first* 4 *distal unfolded leaves*.—About Light Green 142A.
- *Average intensity of anthocyanin coloration of six distal leaves prior to flowering*.—Absent or very slight.
- *Density of prostrate hairs between veins at lower surface of* 4*th distal unfolded leaf*.—Absent or very sparse.
- *Density of erect hairs between veins at lower surface of* 4*th distal unfolded leaf*.—Absent or very sparse.
- *Density of prostrate hairs on veins at lower surface of* 4*th distal unfolded leaf*.—Absent or very sparse.
- *Density of erect hairs on veins at lower surface of* 4*th distal unfolded leaf*.—Absent or very sparse.

Mature leaves (observations made in the middle third of shoot):

- *Size*.—Large.
- *Average length*.—Approximately 10 cm to 12 cm.
- *Average width*.—Approximately 13 cm to 15 cm.
- *Shape of blade*.—Pentagonal.
- *Number of lobes*.—Approximately 5.
- *Mature leaf profile*.—Undulate.
- *Blistering surface of blade upper surface*.—Absent or very weak.
- *Leaf blade tip*.—In the plane of the leaf.
- *Undulation of margin*.—Slightly undulating.
- *Thickness*.—Average — typical of *Vitis vinifera* species.
- *Overall shape of teeth*.—Mixture of both sides straight and both sides convex.
- *Length of teeth*.—Medium, ranging from about 5 mm to 10 mm, usually 8 mm.

*Ratio length/width of teeth*.—Very small, nearly 1:1.
*General shape of petiole sinus lobes*.—Wide open.
*Tooth at petiole sinus*.—Absent.
*Petiole sinus limited by veins*.—Absent.
*Shape of upper lateral sinus lobes*.—Open.
*Depth of upper lateral sinuses*.—Deep, approximately 4 cm to 6 cm.
*Density of prostrate hairs between veins on lower surface of blade*.—Absent to very sparse.
*Density of erect hairs between veins on lower surface of blade*.—Absent to very sparse.
*Density of prostrate hairs on main veins on lower surface of blade*.—Absent to very sparse.
*Density of erect hairs on main veins on lower surface of blade*.—Absent to very sparse.
*Density of prostrate hairs on main veins on upper surface of blade*.—Absent to very sparse.
*Autumn coloration of leaves*.—Usually about Light Green 138B becoming about Medium Grey-Brown 199C.

Upper leaf surface:
*Color*.—About Dark Green 141A.
*Surface texture*.—Smooth.
*Surface appearance*.—Dull.
*Anthocyanin coloration of main veins*.—Absent or very sparse.

Lower leaf surface:
*Color*.—About Light Green 141D.
*Surface texture*.—Smooth, dull.
*Surface appearance*.—Dull.
*Anthocyanin coloration of main veins*.—Absent or very low.

Petiole:
*Length of petiole*.—Approximately 5.5 cm.
*Diameter*.—Approximately 3 mm.
*Length of petiole compared to middle vein*.—Much shorter; 5.5 cm for the petiole compared to 11 cm for middle vein.
*Density of prostrate hairs on petiole*.—Absent.
*Density of erect hairs on petiole*.—Absent.
*Color*.—About Light Green 141D.

Buds:
*Shape*.—Conical.
*Size*.—Medium, approximately 3 mm wide×4 mm long.
*Position*.—Slightly held out.
*Bud fruitfulness*.—Basal, mostly fruitful.
*Time of bud burst*.—Early, approximately March 3rd for the southern San Joaquin Valley region of California.

FLOWERS

General:
*Flower type*.—Fully developed stamen and fully developed gynoecium.
*Position of first flowering node*.—Usually $4^{th}$ to $5^{th}$ node of current season growth.
*Number of inflorescences per shoot*.—Averages 1.5.
*Time of full bloom*.—Approximately April 25th in the southern San Joaquin Valley region of California.

FRUIT

General:
*Ripening period*.—Very early season, beginning about July 1st in the southern San Joaquin Valley region of California.
*Use*.—Fresh market.
*Storage quality*.—Excellent.

Cluster:
*Form*.—Broadly conical, shouldered.
*Cluster size* (*peduncle excluded*).—Large.
*Cluster length* (*peduncle excluded*).—Approximately 21 cm.
*Cluster width*.—Approximately 20 cm.
*Cluster weight*.—Approximately 625 g.
*Cluster density*.—Medium, loose-full.
*Number of berries*.—Approximately 70 berries after tipping.

Peduncle:
*Length*.—Long, approximately 3 cm.
*Diameter*.—Approximately 5 mm.
*Lignification of peduncle*.—Weak.
*Color*.—About Medium Green 143B.

Berry:
*Size*.—Large, approximately 8.5 g.
*Dimensions*.—Width: Approximately 23 mm. Length: Approximately 26 mm.
*Uniformity of size*.—Uniform.
*Shape*.—Broad elliptic.
*Cross section*.—Circular.
*Skin color* (*without bloom*).—About Light Green 141D.
*Flesh color*.—About Medium Yellow-Green149B.
*Anthocyanin color of flesh*.—Absent or very weak.
*Bloom* (*cuticular wax*).—Medium, typical of most commercial *Vitis vinifera*.
*Pedicel length*.—Approximately 11 mm.
*Pedicel thickness*.—Medium, approximately 1.2 mm.
*Berry separation from pedicel*.—Moderately easy.
*Seed traces*.—Rudimentary.
*Berry firmness*.—Very firm.
*Flesh juiciness*.—Very juicy.
*Flesh texture*.—Very crunchy.
*Particular flavor*.—Slightly Muscat.
*Refractometer test*.—About 18 Brix.
*Juice pH*.—About 3.56.
*Titratable acidity*.—About 0.41%.
*Brix:acid ratio*.—Approximately 44.

Skin:
*Skin thickness*.—Medium, about 175 μm.
*Skin texture*.—Smooth.
*Skin reticulation*.—Absent.
*Skin tenacity*.—Tenacious to flesh.
*Skin tendency to crack*.—Rare.
*Skin sensitivity to sunburn*.—None.

What is claimed is:

1. A new and distinct variety of grapevine plant as herein illustrated and described.

* * * * *

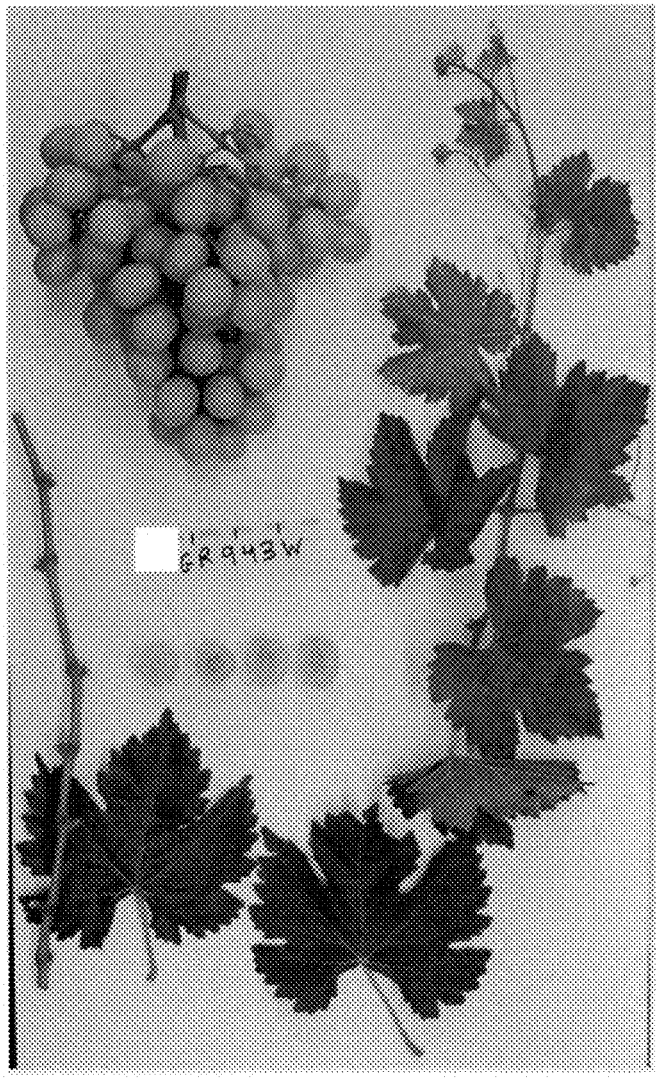
CR943W